United States Patent [19]

Polson

[11] Patent Number: 5,766,124
[45] Date of Patent: Jun. 16, 1998

[54] MAGNETIC STIMULATOR FOR NEURO-MUSCULAR TISSUE

[75] Inventor: Michael John Ross Polson, Narberth, Great Britain

[73] Assignee: The Magstim Company Limited, Whitland, Great Britain

[21] Appl. No.: 608,680

[22] Filed: Feb. 29, 1996

[51] Int. Cl.⁶ .................................................. A61N 1/00
[52] U.S. Cl. ................................................... 600/13
[58] Field of Search ................................... 600/9–15

[56] References Cited

U.S. PATENT DOCUMENTS

| 5,181,902 | 1/1993 | Erickson et al. | 600/13 |
| 5,314,401 | 5/1994 | Tepper | 600/14 |

*Primary Examiner*—John P. Lacyk
*Attorney, Agent, or Firm*—Walter C. Farley

[57] ABSTRACT

A magnetic stimulator of neuro-muscular tissue has a discharge capacitor, at least one discharge control switch for allowing discharge of the discharge capacitor into a stimulating coil and a circuit for recovering energy from the stimulating coil when current flow from the discharge capacitor to the stimulating coil is interrupted, the energy being recovered either by the discharge capacitor or a capacitor additional to the discharge capacitor. The additional capacitor may be a reservoir capacitor connected for charging by a power supply and there may be a circuit for pumping charge from the reservoir capacitor to a transfer capacitor and for pumping charge from the transfer capacitor to the discharge capacitor.

17 Claims, 7 Drawing Sheets

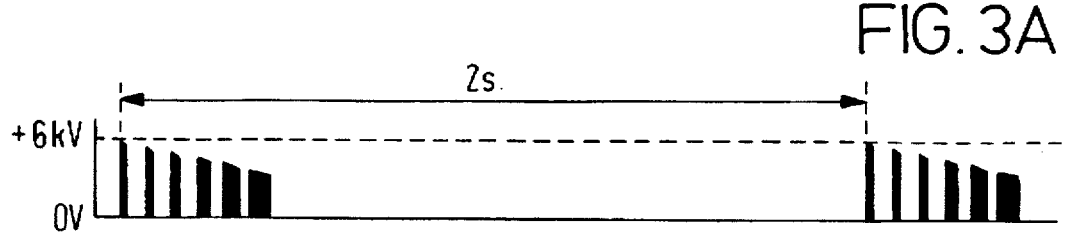
FIG. 3A
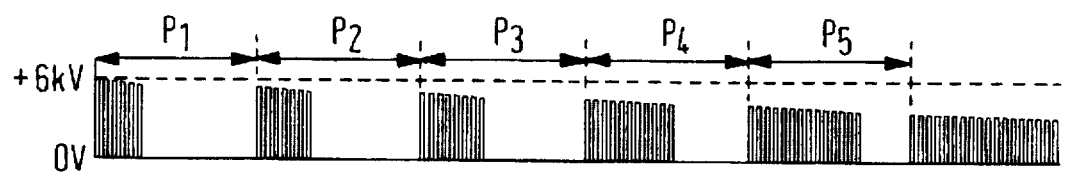
FIG. 3B
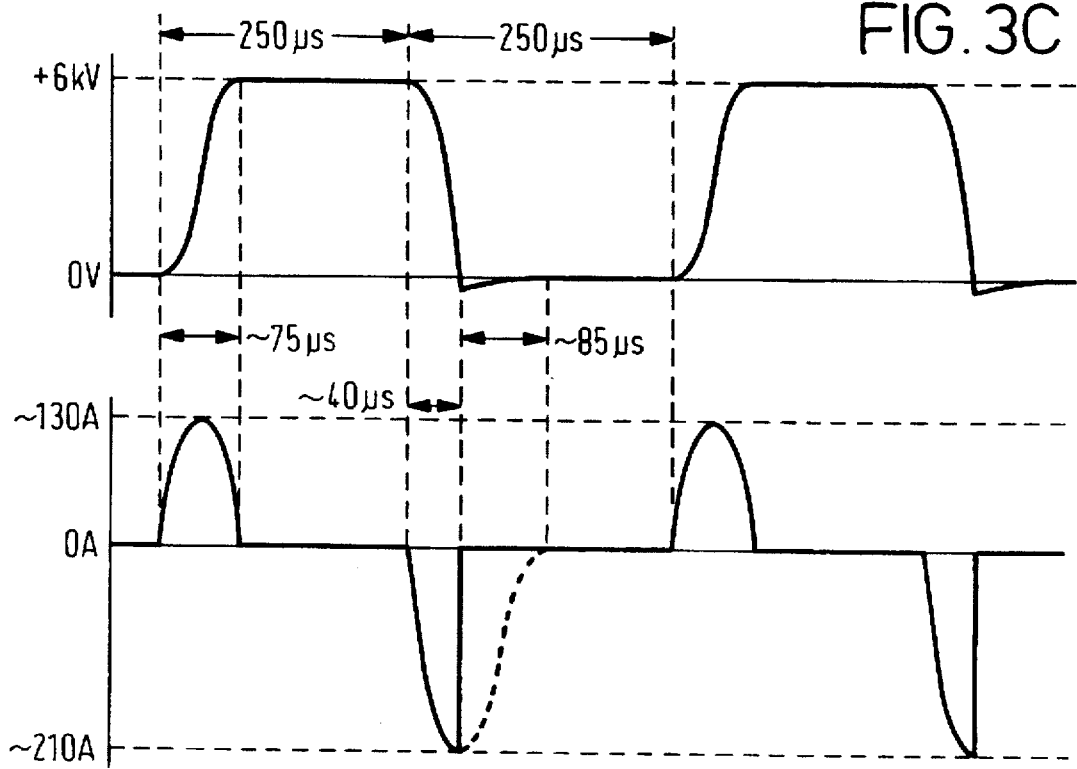
FIG. 3C
FIG. 3D

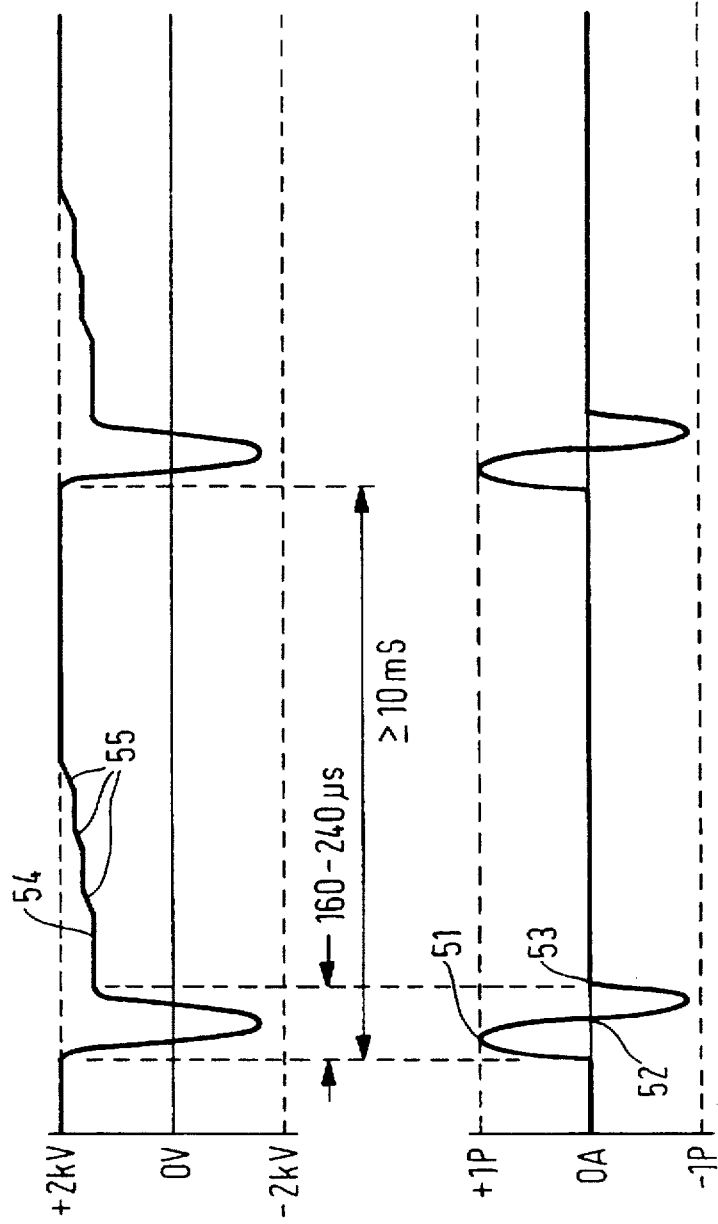

MAGNETIC STIMULATOR FOR NEURO-MUSCULAR TISSUE

FIELD OF THE INVENTION

The present invention relates to the magnetic stimulation of neuro-muscular tissue. The stimulation is achieved by creating a rapidly changing magnetic field, typically of the order of 20 kTesla/sec, in the vicinity of the tissue. An electric current is thereby induced in the tissue and causes stimulation of the tissue.

BACKGROUND TO THE INVENTION

Various forms of magnetic stimulators are known, for example from US-A-4940453.

Known magnetic stimulators comprise generally a charging circuit, a capacitor, a discharge control such as a controlled rectifier for allowing discharge of the capacitor through the stimulating coil and some circuit elements for limiting the effect of undesirable electrical transients. The coil itself may be adapted to fit over a human cranium but may take any of a variety of forms currently known in the art.

Known systems exhibit a variety of disadvantages, particularly the difficulty of achieving any modulation of the magnetic pulse output, a continuously variable high voltage power supply, a large reservoir capacitor and a large instantaneous power output of the high voltage power supply.

The present invention provides a generally more versatile and improved stimulator which reduces at least some of these disadvantages.

SUMMARY OF THE INVENTION

One aspect of the invention is the use of at least one additional capacitor to which charge is supplied or transferred and from which charge is transferred to a discharge capacitor which discharges into the stimulating coil. In one preferred form of the invention charge is pumped under the control of switches from a reservoir capacitor to an intermediate transfer capacitor which is employed to replenish the charge on a capacitor which is controlled to discharge into the stimulating coil. The transfer of charge between successive capacitors may be controlled to occur by way of transient energy storage which may be provided by an inductor or inductors.

The use of at least one additional capacitor enables a substantial increase in the rate of discharge pulses and also a substantial variation in the amplitude of them.

Another aspect of the invention is the controlled recovery of energy from the stimulating coil and in particular means for recovery of energy from the stimulating coil to the discharge capacitor or another capacitor when the current flow from the discharge capacitor to the stimulating coil is interrupted. The other capacitor may be the transfer capacitor, if there is one, or the reservoir capacitor. The recovery of energy from the stimulating coil may be obtained by way of appropriately connected rectifiers or a transformer coupling.

BRIEF DESCRIPTION OF THE DRAWINGS

FIGS. 3A to 3D show waveforms relating to a transfer capacitor;

FIGS. 5A to 5C show waveforms relating to a discharge capacitor in the embodiment shown in FIG. 2;

DETAILED DESCRIPTION OF PREFERRED EMBODIMENTS

Figure 1:
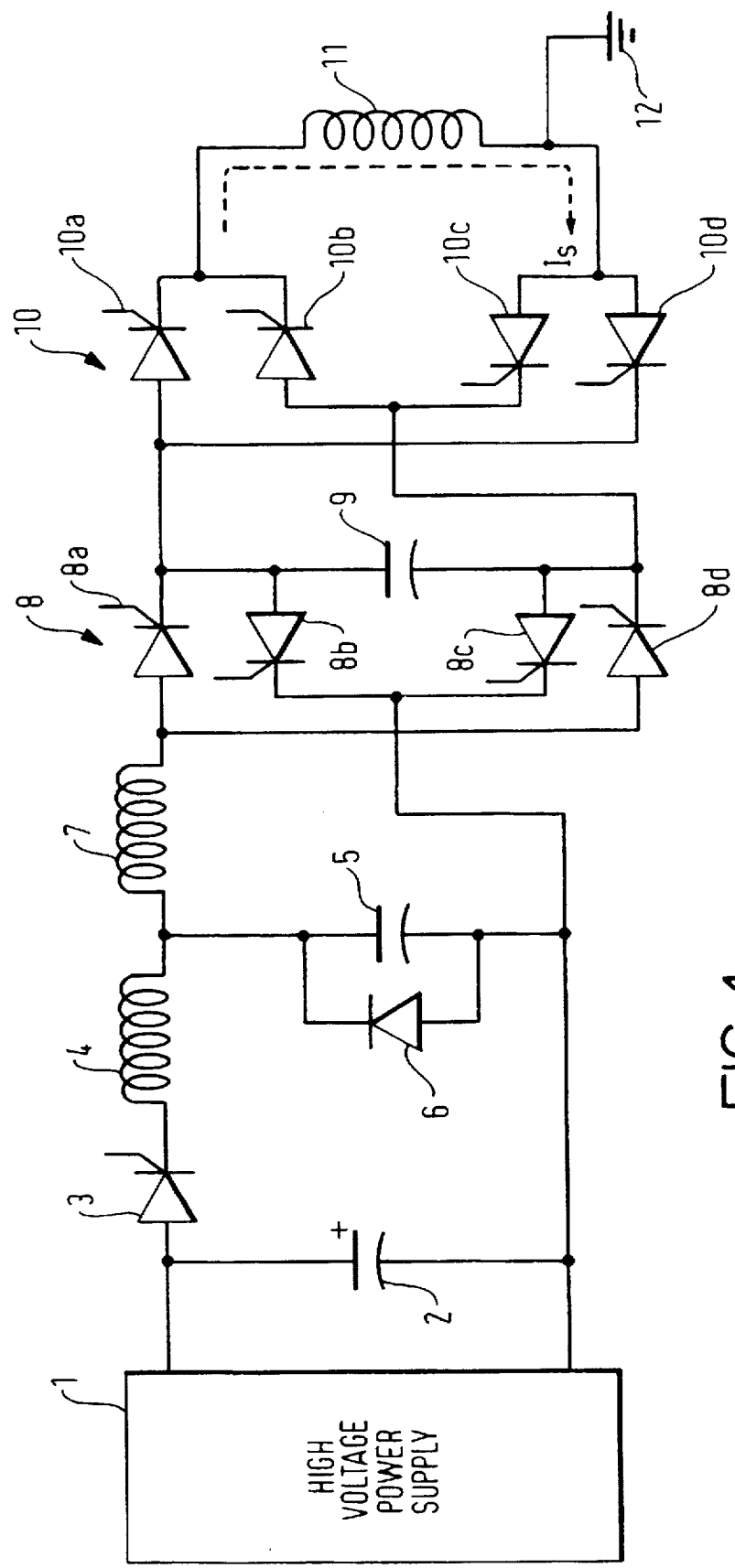
FIG. 1 illustrates one embodiment of a magnetic stimulator according to the invention.

The stimulator shown in FIG. 1 is based on a charge storage capacitor which stores an electric charge which is transferred, preferably by way of an intermediate or 'transfer' capacitor, to another capacitor which is discharged into a stimulating coil. The coil provides in response to the discharge of current through it a high value time-varying magnetic field which induces electric current in neuro-muscular tissue. The design of the stimulating coil is not generally relevant to the present invention and it need not be permanently connected to the remainder of the circuit.

In the embodiment shown, a high voltage power supply 1, which may be of any suitable construction and may be variable, is provided for charging a first capacitor 2, hereinafter called the 'reservoir capacitor'. Discharge of the reservoir capacitor is controlled by a controllable series switch 3, which, like all the other controllable switches in the embodiment, may be a thyristor but could be any of a large variety of suitable switches. The thyristor 3 is connected to a series inductor 4, which is connected to the upper plate of a transfer capacitor 5 of which the lower plate is connected to the lower plate of capacitor 2. A reverse diode 6 is connected across the capacitor 5, the diode blocking current in the direction of normal current flow through the switch 3 and the inductor 4.

The upper plate of the transfer capacitor 5 is connected by way of an inductor 7 to the anodes of two thyristor switches 8a and 8d of which the cathodes are connected to opposite plates of a third or discharge capacitor 9. The inductor 7, like the inductor 4, is a current limiter which is capable of transient energy storage. The lower plate of the transfer capacitor 5 is connected to the cathodes of thyristors 8b and 8c, of which the anodes are connected to the upper and lower plates respectively of the discharge capacitor 9. The upper plate of the capacitor 9 is connected to the anode of a thyristor 10a and the cathode of a thyristor 10d, the cathode of thyristor 10a and the anode of thyristor 10d being connected to upper and lower terminals respectively of the stimulating coil 11. Similarly, the lower plate of the capacitor 9 is connected to the anode of thyristor 10b and to the cathode of thyristor 10c, the cathode of thyristor 10b and the anode of thyristor 10b being connected to the upper and lower terminals of the stimulating coil 11. Thus the thyristors 10a–10d constitute a bridge 10 which determines a unidirectional flow of current through the coil 11 irrespective of the polarity of the voltage across the capacitor 5. In this embodiment the lower terminal of the stimulating coil 11 is provided with a ground connection 12.

It may be seen that the thyristor switch 3 and the capacitor 2 are a means for charging the transfer capacitor 5, the switches are a means for controlling the transfer of charge from the transfer capacitor 5 to the discharge capacitor 9 and the switches 10 are a means for controlling the discharge of the capacitor 9 through the stimulating coil 11. A control circuit for the thyristors is not shown because its operation will be obvious from the description that follows.

The arrangement shown in FIG. 1 preferably operates as follows.

FIG. 3A illustrates the voltage across the transfer capacitor, the voltage waveform of FIG. 3A being shown to an expanded timescale in FIG. 3B and to an even larger scale in FIG. 3C. FIG. 3D illustrates the current flow through the transfer capacitor and, in dashed lines, the current flow through the diode 6.

Figure 4A:
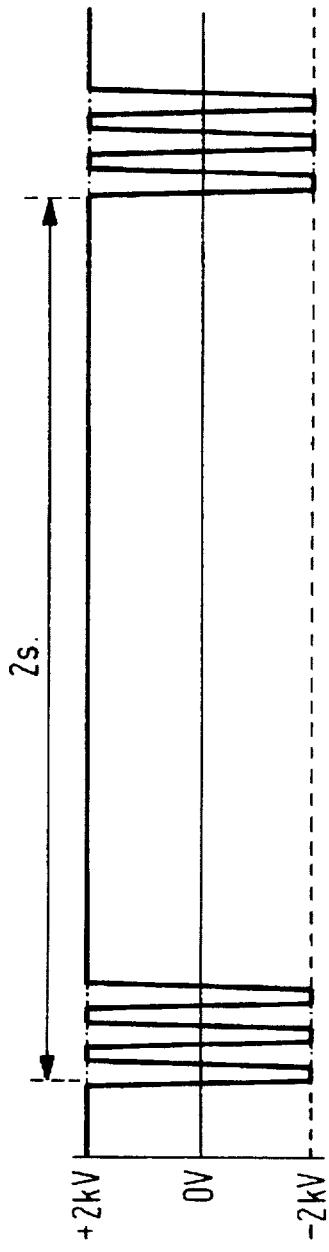
FIGS. 4A to 4C show waveforms relating to a final or discharge capacitor in the embodiment shown in FIG. 1.
Figure 4B:
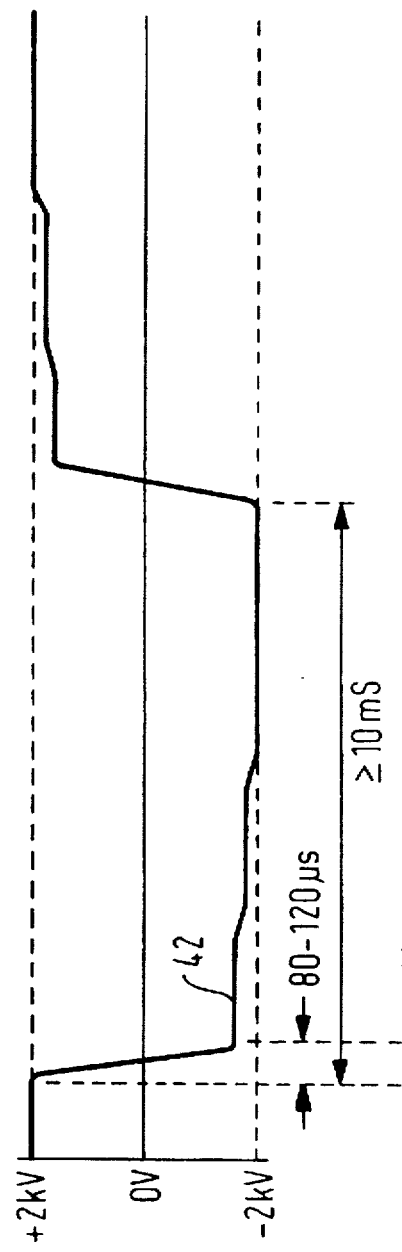
Figure 4C:
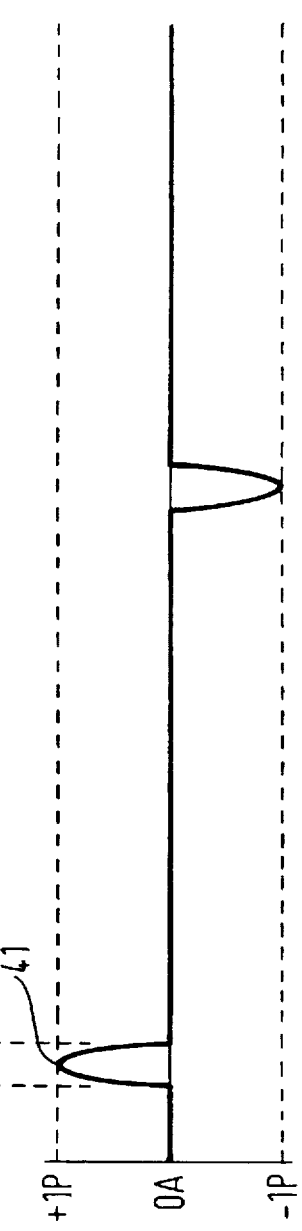

FIG. 4A illustrates the voltage across the discharge capacitor 9, the voltage across the capacitor 9 being shown to a larger timescale in FIG. 4B, and the current flow through the discharge capacitor in FIG. 4C.

Initially, the reservoir capacitor 2 would be charged to a high voltage such as 3 kV and the discharge capacitor 9 would be charged to 1.8 kV, the upper plate being positively charged.

A first pulse stimulus in a train of pulses for the stimulating coil is caused by rendering the switches 10a and 10c conductive, by applying trigger signals to the gates of these thyristors, so that capacitor 9 discharges by way of the loop comprising the thyristor 10a, the stimulating coil 11 and the thyristor 10c. The discharge current reaches its peak value (41 in FIG. 4C) after a quarter of the resonant period of the loop, typically, for example, 40 microseconds, and then begins to diminish. After, for example, 80 microseconds, half the resonant period, the discharge current has diminished to zero. Most of the energy in the loop has been returned to the capacitor 9. At this point, thyristors 10a and 10c stop conducting. The voltage 42 (FIG. 4B) on the discharge capacitor is about 80% of its initial magnitude but the polarity is reversed, the lower plate being positive.

The stimulating pulses are intended to be a minimum of 10 milliseconds apart. During the rest time, the capacitor 9 is replenished so that it is recharged to a selected voltage which may be the same as or different from the initial voltage (1.8 kV). In particular, the thyristor 3 in series with the reservoir capacitor 2 is made conductive, whereby charge is transferred from the reservoir capacitor 2 to the transfer capacitor 5. The series inductor 4 is chosen so that this transfer is complete in a time of the order of 75 microseconds, the peak current being about 130 amps in a typical system. After half of a resonant cycle, the current from the reservoir capacitor has fallen to zero and the thyristor 3 is turned off. The voltage on the transfer capacitor 5 will now be greater than the voltage on the reservoir capacitor owing to the pumping action of the inductor 4.

Next, either the thyristors 8a and 8c are rendered conductive or the thyristors 8b and 8d are rendered conductive, depending on the polarity of the capacitor 9. As mentioned above, after the first pulse, the lower plate is positive so that thyristors 8a and 8c will be rendered conductive. Charge is thereby transferred from the transfer capacitor 5 to the capacitor 9 because the transfer capacitor 5 has been charged to a higher voltage than the discharge capacitor 9. At the point when the voltage at the transfer capacitor 5 has fallen to zero, substantially all the energy previously stored in it is transiently stored in the inductor 7. Current continues to flow through the inductor, the capacitor 9 and the clamping diode 6 until all the energy from the transfer capacitor has been transferred to the capacitor 9. At this point, current in the circuit comprising the transfer capacitor, the inductor 7, the capacitor 9 and the relevant conductive thyristors 8a and 8c has fallen to zero, so that the thyristors 8a and 8c turn off. The recharge cycle then repeats by means of triggering the thyristor 3 in series with the reservoir capacitor. In the next cycle, in order to transfer charge between the transfer capacitor 5 and the capacitor 9, the thyristors 8b and 8d will be rendered conductive.

In practice the replenishment cycle of operation may be repeated a multiplicity of times.

Once the discharge capacitor 9 has been recharged, the next stimulus in the train of stimuli can be delivered by triggering the switches 10b and 10d so that the direction of current flow in the path of the second stimulus is the same as that for the first stimulus, for which the thyristors 10a and 10c are made conductive.

In the second embodiment, shown in FIG. 2, some parts, shown by like reference numerals, are common to the embodiment already described with reference to FIG. 1. Thus the reservoir capacitor 2 is charged from the high voltage supply 1 and can be discharged by means of the controlled switch 3 by way of the inductor 4 into the transfer capacitor 5, from which charge can be transferred to the discharge capacitor by way of the inductor 7 when the thyristor 8e is rendered conductive. The discharge capacitor 9 may be discharged through the stimulating coil 11 by way of thyristor 10e. In anti-parallel with the thyristor 10e is a diode rectifier 12.

Figure 2:
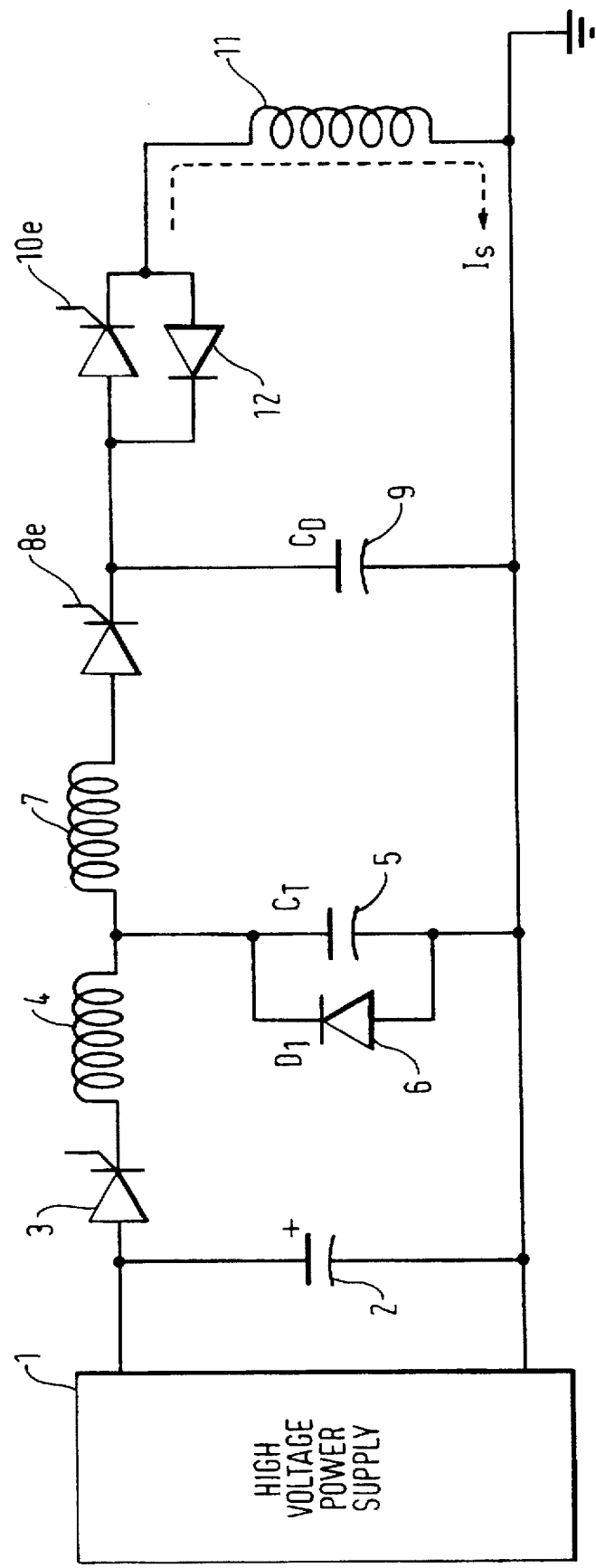
FIG. 2 illustrates a second embodiment of a magnetic stimulator according to the invention.

The preferred method of operation of the embodiment shown in FIG. 2 is as follows. FIG. 5A shows the waveform of the voltage across the capacitor 9, FIG. 5B shows this waveform to a larger timescale and FIG. 5C shows the current through the capacitor 9.

Initially, the reservoir capacitor 2 may be charged, for example to 3 kV, and the capacitor 9 may be charged to 1.8 kV, the upper plate being positive.

The first stimulus is delivered by rendering thyristor 10e conductive so that the discharge current Is starts to flow in the stimulating coil 11. The current reaches a peak value 51 after about a quarter of the resonant period and then starts to fall. After half the resonant period, in this example 80 microseconds, the current has reduced to zero (point 52, FIG. 5C) and most of the energy has been returned to the capacitor 9. At this point, the diode becomes forward biased, allowing the second part of the resonant cycle to follow. The current flows in the opposite direction and at the end of the cycle the current to the capacitor 9 has again fallen to zero (point 53), and the diode 12 is reversed biased. No further current can flow because the thyristor switch 10e has been turned off. The voltage 54 (FIG. 5B) on the capacitor 9 is typically about 65% of its original magnitude, and has the original polarity.

The stimuli may be a minimum of, for example, 10 milliseconds apart and during the inter-pulse period the capacitor 9 is replenished by means of rendering the thyristor switch 3 conductive, so that charge is transferred from the reservoir capacitor 2 to the transfer capacitor 5. The series inductor is chosen such that the charge transfer lasts about 75 microseconds, the peak current being typically about 130 amps. After half a resonant cycle, this charge current from capacitor 2 has fallen to zero and the thyristor 3 turns off. The voltage on the transfer capacitor 5 is now higher than the reservoir voltage owing to the pumping action of the inductor. Next, the thyristor 8 is triggered so as to render this thyristor switch conductive. Thereby charge is transferred from the transfer capacitor 5 to the discharge capacitor 9, because the transfer capacitor is charged to a higher voltage than the capacitor. At the point when the voltage on the transfer capacitor 5 has fallen to zero virtually all the energy in the loop comprising the two capacitors 5 and 9, the inductor 7 and the thyristor 8e is stored transiently in the inductor 7. The current continues to flow by way of the diode 6 until all the energy has been transferred into the capacitor 9. At this point the current has again fallen to zero and the thyristor 8e is turned off. The recharge cycle is repeated by triggering the thyristor switch 3 until sufficient charge has been transferred to replenish the capacitor 9. Again, although only a few recharge cycles 55 are shown in FIG. 5B, in practice there may be a greater number of recharge cycles, for example twenty.

When the discharge capacitor 9 has been recharged, the next stimulus in the train may be delivered by the triggering of the thyristor 10e.

The embodiment shown in FIG. 2 is simpler than that shown in FIG. 1 but is less efficient, and requires two voltage reversals instead of one for each discharge of the capacitor 9.

The embodiments shown in FIGS. 1 and 2 are in practice capable of providing variable length trains of pulses within successive periods P1, P2 etc (FIG. 3A) which have high repetition rates, such as 100 Hz, and can be amplitude modulated, typically about 20%, and/or frequency modulated without requiring multiple parallel discharge systems or a variable high voltage power supply with high instantaneous power output. For example, recharging a 70µF capacitor to 1.8 kV in 10 microseconds requires about 11 kW whereas the preferred embodiment could utilize a 500 VA transformer in the supply unit 1.

Figure 6:
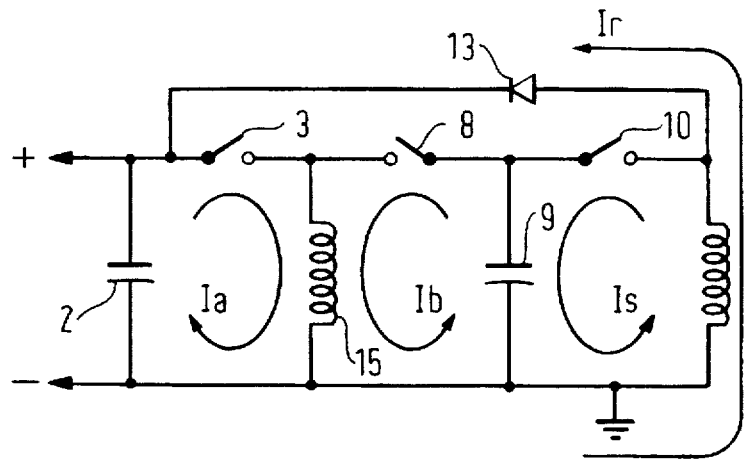
FIG. 6 illustrates another embodiment of the invention.

FIG. 6 illustrates an embodiment which generally resembles that shown in FIG. 1 because it has a reservoir capacitor 2 connected to a high voltage power supply, and a discharge capacitor 9 which is controllable to discharge into the stimulating coil 11 when the switch 10 is closed. However, in place of the transfer capacitor is a transfer inductor 15 which acts to store energy transiently during energy transfer between the reservoir capacitor 2 and the discharge capacitor 9.

The transfer inductor 15 forms distinct loops with the capacitor 2 and the capacitor 9, these loops containing respective switches 3 and 8. A rectifier 13 is coupled to convey energy unidirectionally from the stimulating coil back to the reservoir capacitor 2 in response to the interruption of the flow of current between the capacitor 9 and the coil 11.

In the circuit shown in FIG. 6, the high voltage supply continually supplies a charging current to the reservoir capacitor 2, maintaining its voltage close to a selected maximum. The discharge capacitor 9 is charged to a required level as follows. The switch 3 is closed, allowing current Ia to flow in the transfer inductor 15. When this current reaches some predetermined value, the switch 3 is opened and switch 8 closed simultaneously, the current Ib in the transfer inductor 15 charging the capacitor 9. The switch 8 may be opened when the current in the respective loop has decayed to zero. A stimulating pulse can be delivered by the closure of the switch 10. When the current Is in the coil is near a peak value, the switch 10 may be opened, allowing a current Ir to flow by way of the back-coupling diode 13 to charge the reservoir capacitor 2. The arrangement enables the reservoir capacitor's voltage to be lower than the discharge capacitor's voltage and the control of the energy transferred to the discharge capacitor 9 for each cycle. Furthermore, the discharge capacitor does not experience significant voltage reversal.

Figure 7:
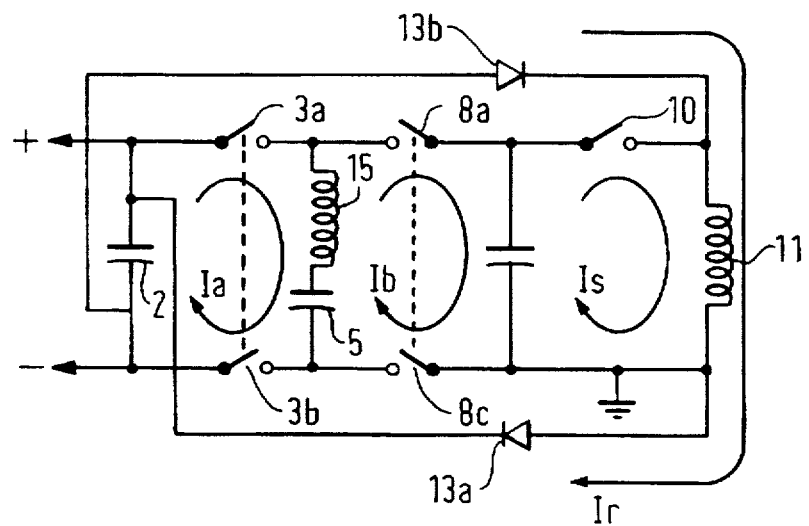
FIG. 7 illustrates a modification of the embodiment shown in FIG. 6.

FIG. 7 illustrates an embodiment which uses both a transfer capacitor 5 and a transfer inductor between the reservoir capacitor 2 and the discharge capacitor 9. In this embodiment, the branch containing the transfer inductor 15 in FIG. 6 contains the transfer capacitor 5 in series with inductor 15. Ganged series switches 3a, 3b are disposed between the reservoir capacitor 2 and the transfer branch and ganged switches 8a, 8c are disposed between the transfer branch and the discharge capacitor. Opposite ends of the stimulating coil are connected by the diode rectifiers 13a and 13b to respective plates of the reservoir capacitor 2 so that current flowing in the stimulating coil after closure of the discharge control switch 10 can flow to charge the reservoir capacitor 2 when the switch 10 is opened, as described above with reference to FIG. 6. The transfer inductor 15 in FIG. 7 may be much smaller than that required for the circuit of FIG. 6 because it acts substantially only as a current limiter. Otherwise the circuit operates similarly to that shown in FIG. 6. The switches 3 and 8 switch only when current flow is zero and may comprise thyristors.

Figure 8:
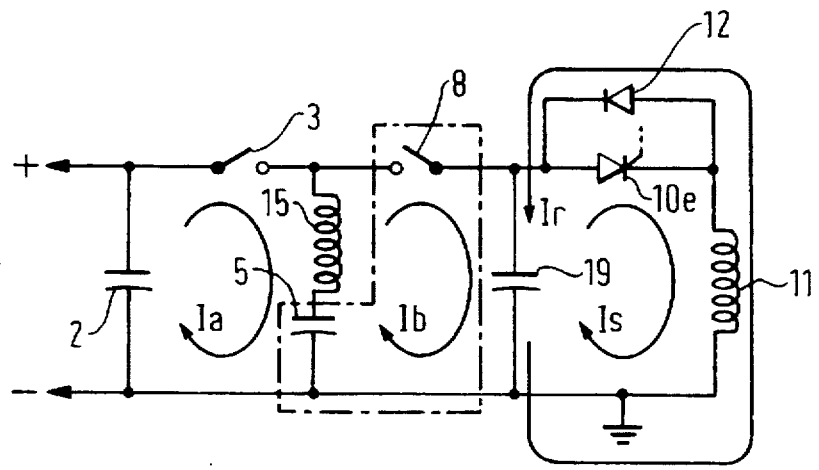
FIG. 8 illustrates another embodiment of the invention, generally resembling the embodiment shown in FIG. 2.

FIG. 8 illustrates an embodiment in which the transfer of charge from the reservoir capacitor 2 to the discharge capacitor 9 resembles that occurring in the embodiment shown in FIGS. 1 and 2. Charge may be pumped by the closing and opening of switch 2 to the transfer capacitor 5 and charge may be pumped from the transfer capacitor 5 to the discharge capacitor 9. The discharge loop resembles that described with reference to FIG. 2, the thyristor 10e allowing discharge of the discharge capacitor 9 into the stimulating coil 11 and the diode 12 allowing reverse flow of charge back to the discharge capacitor in response to the cessation of current flow around the discharge loop, as previously described. This embodiment, like the embodiments in FIGS. 1 and 2, may employ thyristors for all the controlled switches because all the switching may occur when the resepctive current is zero.

FIG. 8 may be modified by the removal of capacitor 5 and switch 8 shown within the chain-line; the inductor 15 then needs to be in series between the switch 3 and the discharge capacitor 9.

Figure 9:
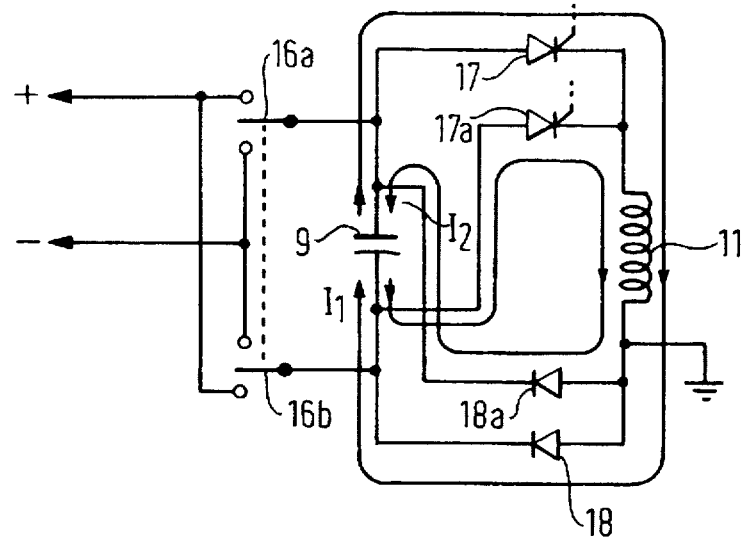
FIG. 9 illustrates an embodiment which provides for recovery of energy back to the discharge capacitor.

FIG. 9 illustrates a somewhat different embodiment which may include a reservoir capacitor 2 and a transfer capacitor 5 as previously described but which may be arranged, as shown, such that the discharge capacitor 9 is connected to the high voltage supply by way of ganged switches 16, 16a that enable reversal of the supply voltage applied to the discharge capacitor. The discharge capacitor is connected to the stimulating coil 11 by way of a rectifying bridge containing two controlled rectifiers 17, 17a, and two diode rectifiers 18, 18a. Once the capacitor 9 has been charged to the required energy level, the controlled rectifier 17 may be made conductive, so that current I1 flows in the coil 11. The current reaches a maximum after a time determined by the resonant frequency of the discharge loop comprising the capacitor 9 and the coil 11. The current decreases to zero, at which point the controlled rectifier 17 can be switched off. The voltage on the capacitor 9 is now reversed and the next discharge requires the firing of controlled rectifier 17a, allowing current I2 to flow in the coil in the same direction as during the previous cycle. The discharge capacitor 9 recovers a substantial portion of the energy held at the start of a cycle and needs only replenishment, rather than a full charging cycle, from the supply by means of the two-pole two-way switches 16, 16a, the operation of the switches being selected to connect the supply in the correct polarity to the capacitor 9.

Figure 10:
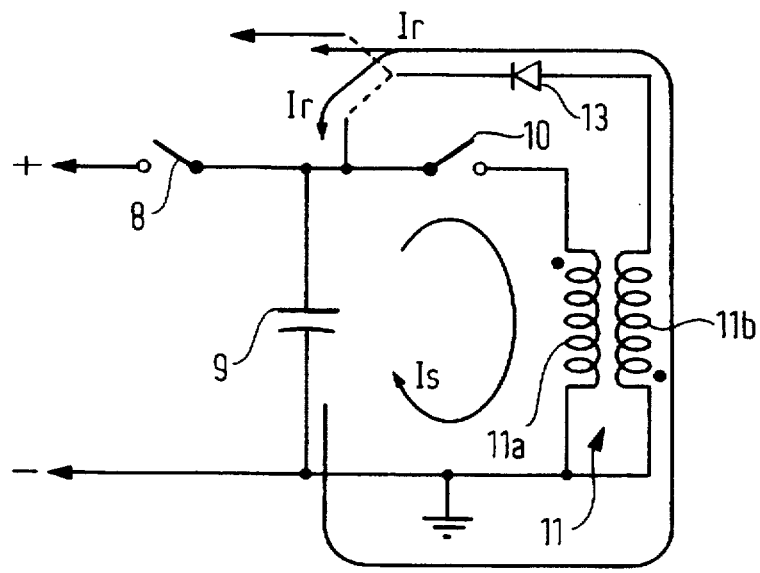
FIG. 10 illustrates an embodiment employing a stimulator coil forming part of a transformer.

FIG. 10 illustrates a modification which may employ any of the energy transfer techniques described with reference to FIGS. 1 to 8. The relevant components, including the high voltage supply and the reservoir capacitor, have been omitted from FIG. 10 for the sake of simplicity.

In the modification shown in FIG. 10, charge is transferred to the discharge capacitor 9 by means of closure of the switch 8. Closure of the switch 10 allows discharge of the capacitor 9 into the stimulating coil 11, which comprises two interleaved windings 11a, 11b acting as a transformer. When the current in winding 11a is at or near a maximum, the switch 10 may be opened. The cessation of current flow in the primary winding 11a induces a flow of current in the secondary winding 11b. This current may be used to recharge by way of the diode 13 the discharge capacitor 9 or the reservoir capacitor (if there is one), so that energy is recovered from the stimulating coil.

All the foregoing embodiments include means enabling the recovery of energy from the stimulating coil to a charge storage capacitor when a discharge control switch between the discharge capacitor and the coil is opened or made non-conductive so as to interrupt current flow from the discharge capacitor to the stimulating coil.

Figure 11:
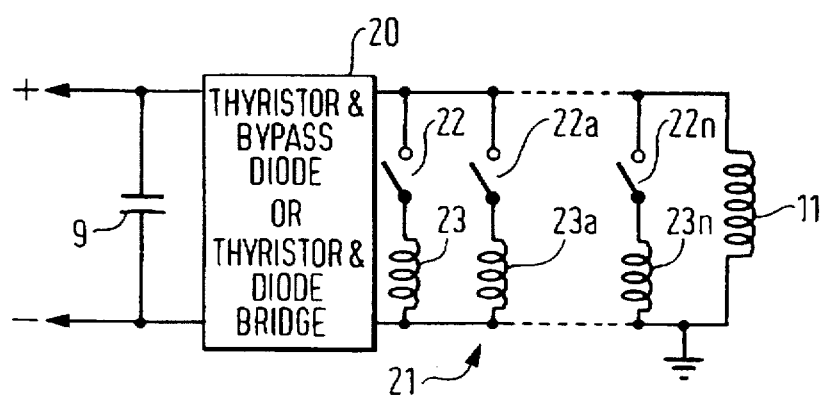
FIG. 11 illustrates an embodiment which employs inductors for controlling the discharge of energy into the stimulating coil.

FIG. 11 illustrates another embodiment of the invention, which is intended to be a modification of the circuit shown in either FIG. 8 or FIG. 9. In this embodiment, the discharge capacitor 9 may have charge coupled to it either directly from the power supply or indirectly by means of a reservoir capacitor and, if desired, a transfer capacitor as previously described with reference to the preceding Figures. Between the discharge capacitor 9 and the stimulating coil 11 is a network 20 which may be, for example, either a controlled rectifier switch and a by-pass diode, as shown in FIG. 8 or a thyristor and diode bridge as shown in FIG. 9.

Additionally, the stimulating coil 11 is in parallel with a ladder network 21 comprising a plurality of parallel branches each containing an inductor 22, 22a ... 22n and a respective switch 23, 23a ... 23n. Preferably the inductances of the branches of the ladder network increase according to powers of two.

Initially the discharge capacitor would be charged to a much higher energy level than is required for a first pulse in a series and all the inductors 22, 22a etc may be switched into parallel connection with the stimulating coil. During the first discharge, the energy that was stored in the capacitor 9 is divided between the stimulating coil and the inductor network in proportion to the ratio of the respective inductance values. The discharge cycle proceeds as described with reference to FIG. 8 or FIG. 9, terminating with the storage of recovered energy in the capacitor 9. Because the circuit components are imperfect, some of the energy will have been lost so there will be less energy in the capacitor at the end of the cycle than there was at the beginning. Before the initiation of the second pulse in the train, some of the inductors in the network are switched out of circuit, so that when the discharge takes place, a greater proportion of the capacitor energy is directed into the stimulating coil. This process is repeated for each pulse in the train, such that the value of inductance in parallel with the stimulating coil progressively decreases and the same absolute energy is delivered to the coil during every pulse in the chain. This circuit does not require the discharge capacitor to be 'topped up' between pulses and thereby reduces stresses on the power supply. However, a control circuit for the switches 23, 23a ... 23n has to calculate the appropriate parallel inductance changes for different stimulating coils with a range of inductances and energy losses.

I claim:

1. A magnetic stimulator of neuro-muscular tissue comprising a stimulating coil, a discharge capacitor, means for controlling discharge of said discharge capacitor into said stimulating coil, a reservoir capacitor, and means for pumping charge from said reservoir capacitor to said discharge capacitor.

2. The stimulator of claim 1 wherein said means for pumping comprises an energy storage device, switch means for discharging said reservoir capacitor into said energy storage device and means for transferring energy from said storage device to said discharge capacitor.

3. The stimulator of claim 1 wherein said means for pumping comprises
   an energy storage device;
   a first electrical loop including said energy storage device, said reservoir capacitor and a first controllable switch; and
   a second electrical loop including said energy storage device, said discharge capacitor and a second controllable switch.

4. The stimulator of claim 3 wherein said energy storage device comprises an inductor.

5. The stimulator of claim 3 wherein said energy storage device comprises a transfer capacitor.

6. The stimulator of claim 5 wherein each of said first and second electrical loops includes an inductor.

7. The stimulator of claim 1 further comprising a ladder network in parallel with said stimulating coil, said ladder network having a plurality of branches each including an inductor in series with a controllable switch.

8. The stimulator of claim 1 wherein said means for controlling comprises a switch operative to interrupt current flow from said discharge capacitor to said stimulating coil, and further comprises means operative when current flow from said discharge capacitor to said stimulating coil is interrupted to recover energy from said stimulating coil.

9. The stimulator of claim 8 wherein said means for recovering is coupled to said discharge capacitor.

10. The stimulator of claim 9 wherein said means for recovering comprises a unidirectional connection from said stimulating coil to said discharge capacitor.

11. The stimulator of claim 8 wherein said means for recovering is coupled to said reservoir capacitor.

12. The stimulator of claim 8 wherein said means for recovering comprises a unidirectional connection from said coil to said reservoir capacitor.

13. The stimulator of claim 8 wherein said means for recovering comprises a transformer including said stimulating coil as a primary winding and having a secondary coil coupled to recharge said discharge capacitor or said reservoir capacitor.

14. A magnetic stimulator of neuro-muscular tissue, comprising:
   a stimulating coil;
   a discharge capacitor;
   means for controlling the discharge of the capacitor into the stimulating coil;
   a reservoir capacitor;
   means for pumping charge from the reservoir capacitor to the discharge capacitor; and
   means responsive to interruption of current flow from the discharge capacitor to the stimulating coil for recovering energy from the stimulating coil and for storing energy thereby recovered.

15. The stimulator of claim 14 wherein the means for recovering and storing includes said reservoir capacitor.

16. The stimulator of claim 14 wherein the means for recovering and storing includes said discharge capacitor.

17. A magnetic stimulator of neuro-muscular tissue comprising:

a stimulating coil;

a discharge capacitor;

first means for controlling discharge of said capacitor into said stimulating coil, said first means including a discharge control switch for connecting said capacitor to said stimulating coil and for interrupting flow of current from said discharge capacitor to said stimulating coil;

a reservoir capacitor;

second means for pumping charge from said reservoir capacitor to said discharge capacitor; and third means operative on interruption of current flow from said discharge capacitor to said stimulating coil for recovering energy from said stimulating coil and for storing energy thereby recovered.

* * * * *